United States Patent [19]

Sicurelli, Jr.

[11] Patent Number: 4,608,974
[45] Date of Patent: Sep. 2, 1986

[54] TONGUE THERAPY DEVICE
[76] Inventor: Robert J. Sicurelli, Jr., 1990 E. 4th St., New York, N.Y. 11223
[21] Appl. No.: 790,267
[22] Filed: Oct. 22, 1985
[51] Int. Cl.$^4$ .......................... A61F 5/56; A61F 13/00
[52] U.S. Cl. ................................... 128/136; 128/132 R
[58] Field of Search .................... 128/1 R, 132 R, 136, 128/76 R

[56] References Cited
U.S. PATENT DOCUMENTS

| | | | |
|---|---|---|---|
| 1,405,689 | 2/1922 | Heatwole | 128/136 |
| 3,277,892 | 10/1966 | Tepper | 128/136 |
| 3,312,216 | 4/1967 | Wallshein | 128/136 |
| 3,522,805 | 8/1970 | Wallshein | 128/136 |
| 3,871,370 | 3/1975 | McDonald | 128/136 |
| 3,884,226 | 5/1975 | Tepper | 128/136 |

Primary Examiner—Richard T. Stouffer
Assistant Examiner—Kathleen D'Arrigo
Attorney, Agent, or Firm—Frishauf & Partners

[57] ABSTRACT

A tongue therapy device is disclosed for training the tongue to assume its proper posture on the palate and to prevent tongue thrust during swallowing. The device includes an element, such as a pin, for irritating the tongue upon contact. A protective element is provided which keeps the tongue off the irritating element unless the tongue moves beyond a given point. The protective element can be a resiliently yieldable cover for the pin. Alternatively, it can be a ramp sloped to resist forward movement of the tongue. Each device is compact enough to fit on the lingual side of a single tooth. It can be, therefore, mass-produced to fit substantially all individuals and can be installed relatively quickly and easily.

27 Claims, 27 Drawing Figures

ORIENTATION FIGURE

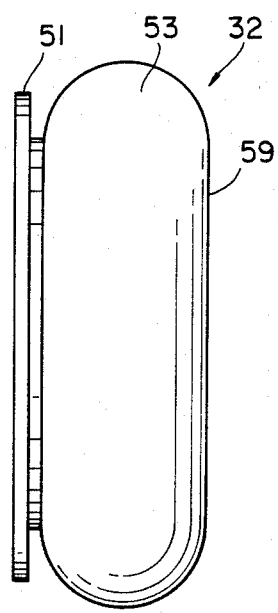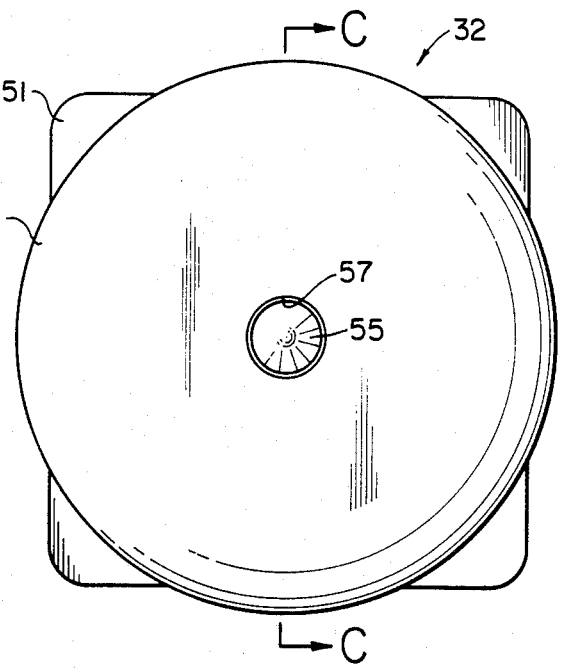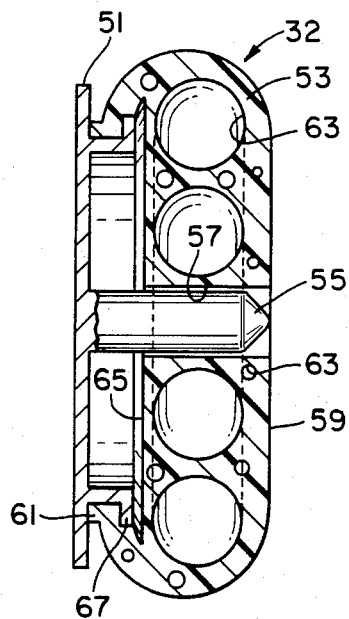
FIG.3A    FIG.3B
FIG.3C

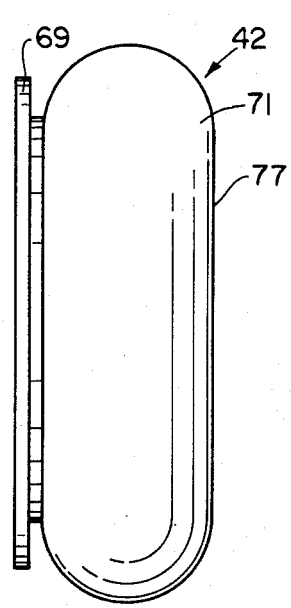
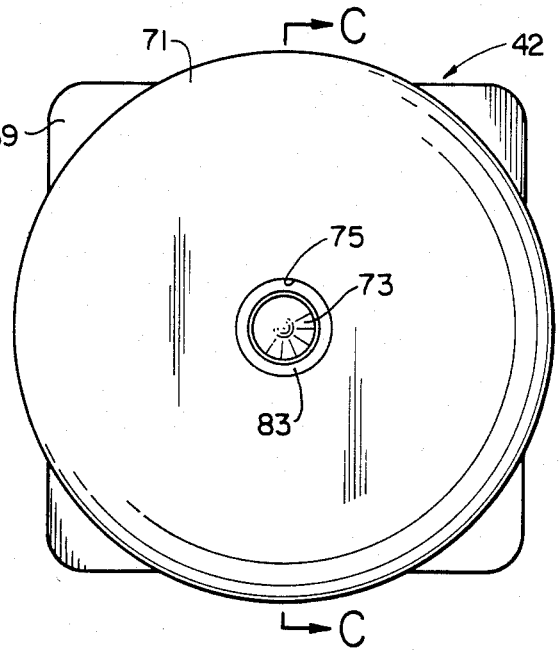
FIG.4A    FIG.4B
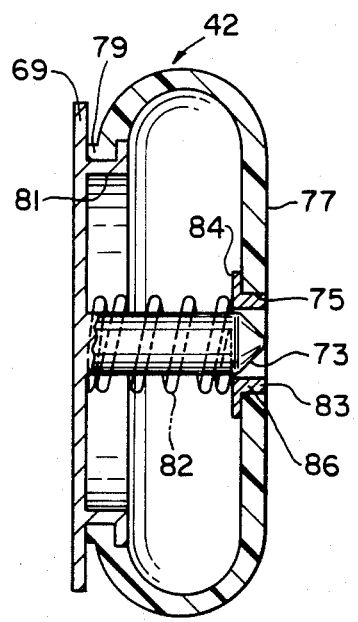
FIG.4C

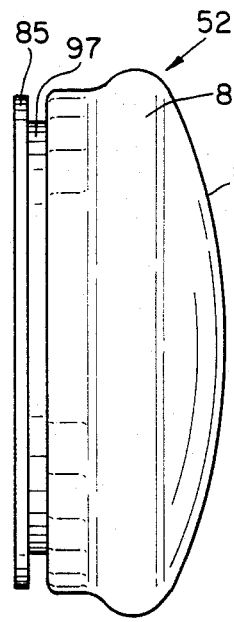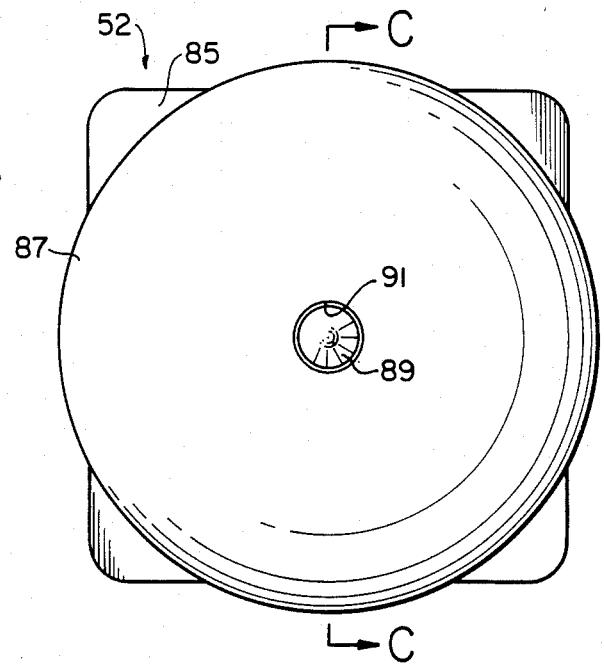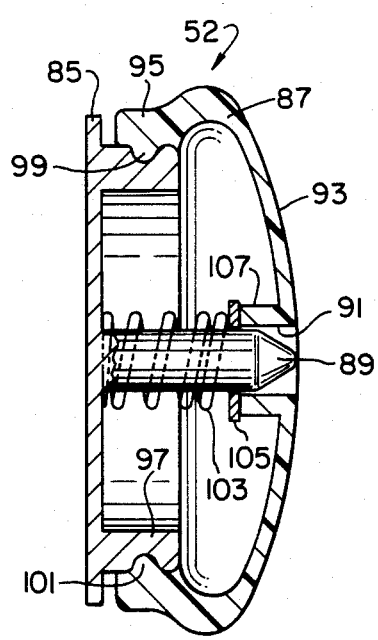
FIG.5A    FIG.5B
FIG.5C

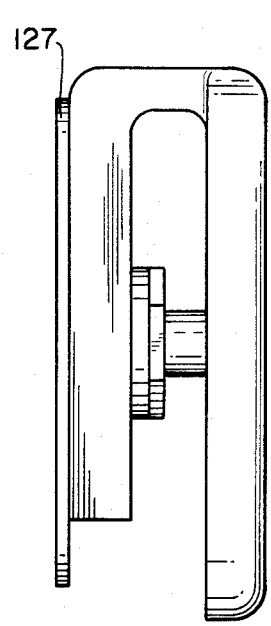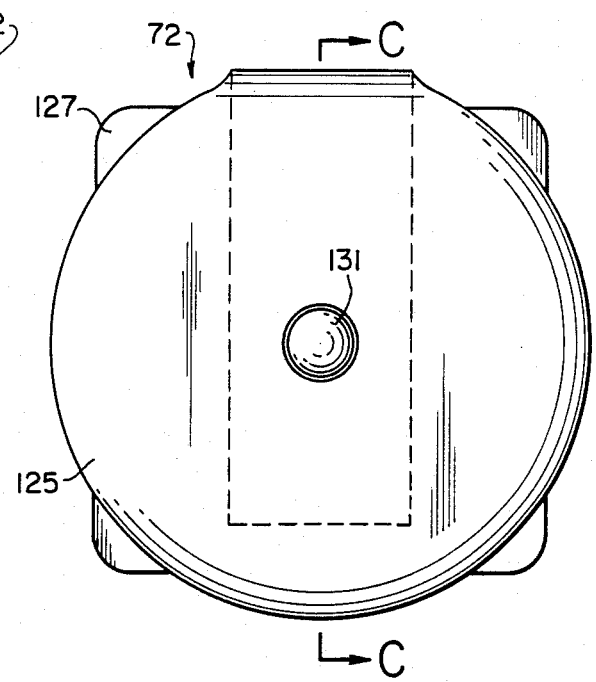
FIG.7A  FIG.7B
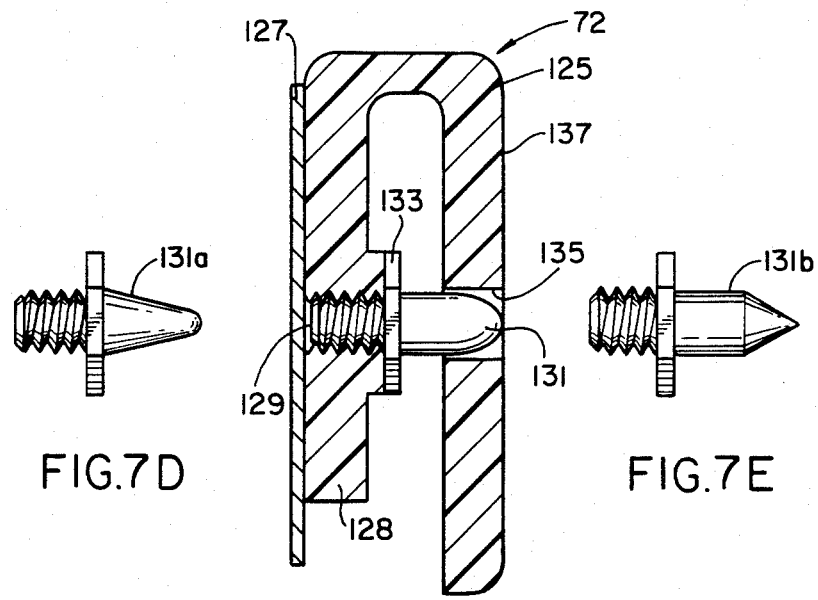
FIG.7D  FIG.7C  FIG.7E 4,608,974

TONGUE THERAPY DEVICE

BACKGROUND OF THE INVENTION

This invention is directed to a tongue therapy technique and, more particularly, to a device for eliminating tongue thrust against the upper teeth during swallowing as well as for training the tongue to assume its correct, normal position in the mouth conforming to the palate.

Malocclusion of the teeth can be caused by a number of factors. Among these is one which is due to the pressure exerted by the tongue on the teeth because of misplacement of the tongue at its rest position as well as tongue movement during the act of swallowing. While at rest, the tongue should adopt a contour like that of the palatal vault. When it does assume this position and shape, then its tip extends only to the palatal rugae (the wrinkled part at the upper, front portion of the palate). However, if out of bad habit, i.e. reverse swallowing, the tongue assumes a different position and shape, it is then likely that the tongue would be positioned to come into forceful contact with the teeth. In addition to the tongue placement-and-shape aspect, the tongue thrusts forward between 500 and 1000 times a day during swallowing. This plunger-like action applies significant forces to the teeth. If the tongue bears against the teeth during one or both of these situations, the force it exerts can result in various dental malocclusions such as anterior open bite and spacing between the teeth.

One technique which has been developed to overcome this abnormal swallowing habit involves the use of a "tongue crib". This device makes use of a plurality of spurs connected together and affixed on the lingual side of the upper teeth to form a fence-like arrangement. It acts as a barrier to prevent the tongue from making contact with the upper teeth. Such an appliance has been used and found to function adequately. See "Control of Abnormal Habits", in Orthodontics, Principles & Practice, W. B. Saunders, Copyright 1972 by T. M. Graber pages 688–693.

Despite the adequacy of this approach, it is unsatisfactory because the appliance is custom-fitted for each individual. This is essential because it must be shaped to fit the shape of the individual's mouth, and it must be sized so it can be attached to the molars. Several disadvantages accrue from the need to custom fit the appliance. Firstly, the appliance is expensive because it requires multiple office visits, cannot be mass produced, and must be expertly and precisely made. Secondly, the patient is discomfitted because a mold impression must be made of the teeth. Thirdly, much time is required for the entire process which includes taking the mold, manufacturing the appliance and installing it. Fourthly, it restrains the tongue from the passive movements of speech and eating by merely retraining as opposed to training. This time could be put to better use in correcting the problem were an alternative appliance available. Fifthly, it prevents the patient from enjoying and being able to eat certain foods by virtue of the fact that a "metal strainer" traverses the palate. Sixthly, it is unesthetic; it is readily seen when the patient smiles. It is, therefore, desirable to provide a device which overcomes the above-mentioned disadvantages of the tongue therapy devices now available.

OBJECTS AND SUMMARY OF THE INVENTION

It is a general object of the invention to provide a device for training the tongue to assume its proper position at rest and during swallowing.

A more specific object of the invention is to provide a tongue therapy device which can be mass produced to fit substantially all individuals.

Another object of the invention is to allow freedom of tongue movements, but *not* during swallowing.

Another object of the invention is to provide a tongue therapy device which is effective yet can be simply and quickly installed.

Another object of the invention is to provide a device which is esthetic and not readily visible.

Another object of the invention is to allow the patient to enjoy eating any food type.

Yet another object of the invention is to provide a tongue therapy device which is relatively inexpensive.

These and other objects of the invention are attained with a device having a base with a face which is attachable to the lingual side of a tooth. On its other, lingual face the base carries an irritating element, such as a pin, which causes discomfort to the tongue when the two come into contact. A protective element is also carried on this face of the base and it normally shields the tongue from the irritating element. However, when the tongue moves in the mouth to extend beyond its proper position, such as during swallowing, the protective element no longer functions as a shield, the tongue then contacts the irritating element, and discomfort results causing withdrawal of the tongue away from the pin and toward its proper position.

One specific embodiment of the invention includes a pin covered by a cushion having a resiliently displaceable portion. The tongue contacts the cushion and proceeds to move it should the tongue move to an improper position, whereby the pin is uncovered, and the pin then projects into the tongue. A number of approaches are discussed below involving alternate cushion arrangements.

In another specific embodiment of the invention, the protective element is stationary and lies, when the device is installed on the tooth, between the proper position of the tongue tip (palate rugae) and the irritating element. The protective element is ramp-like in shape so that the tongue thrust must be strong enough to overcome the resistance of the ramp to movement along it before the irritating element can be reached. This embodiment is advantageous in that it has no moving parts and no voids where food and bacteria can collect.

BRIEF DESCRIPTION OF THE DRAWINGS

This invention is directed to a device for training the tongue to assume its proper position while it is at rest as well as during the act of swallowing and is more fully described below in conjunction with the following drawings:

FIGS. 3A, 3B, and 3C show, respectively, the side, elevational and cross-sectional (along line c—c of FIG. 3B) views of a third embodiment of the inventon;

FIGS. 4A, 4B, and 4C show, respectively, the side, elevational and cross-sectional (along line c—c of FIG. 4B) views of a fourth embodiment of the invention;

FIGS. 5A, 5B, and 5C show, respectively, the side, elevational and cross-sectional (along line c—c of FIG. 5) views of a fifth embodiment of the invention;

FIGS. 7A, 7B, and 7C show, respectively, the side, elevational and cross-sectional (along line c—c of FIG. 7B) views of a seventh embodiment of the invention;

FIGS. 7D and 7E show alternate versions of pin 131; and

DETAILED DESCRIPTION OF THE PREFERRED EMBODIMENTS

In order to place the device provided in accordance with this invention into perspective dimensionally and positionally, FIG. 1 shows the upper teeth, 1, tongue 6 and palate 8 as seen from the lingual side (i.e. from inside the mouth). To each tooth which is or may become affected by abnormal tongue action, one such device, 2, is affixed. The shape of device 2 and its perferred dimensions will discussed in detail below. Suffice it to say at this point, however, that it fits and is placed generally in the manner shown.

Figure 1A:
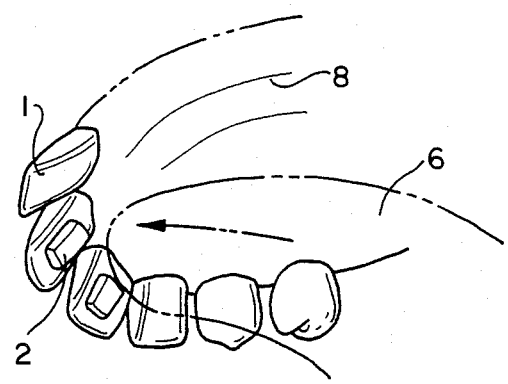
FIG. 1A is an orientation drawing in perspective showing where the device of the invention is placed on the teeth.
Figure 1D:
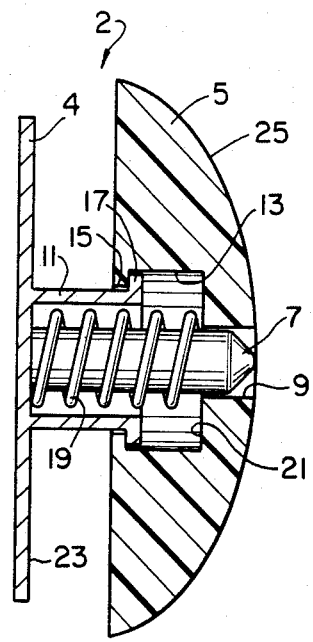
FIGS. 1B, 1C, and 1D show, respectively, the side, elevational and cross-sectional (along line c—c in FIG. 1C) views of a first embodiment of the invention.
Figure 1B:
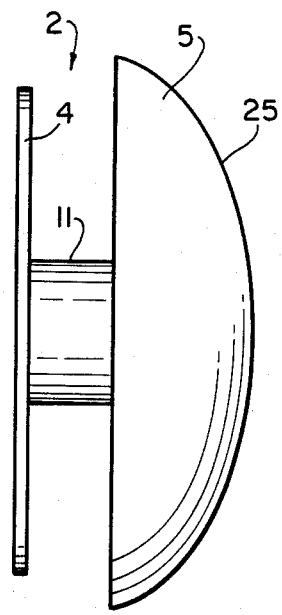
Figure 1C:
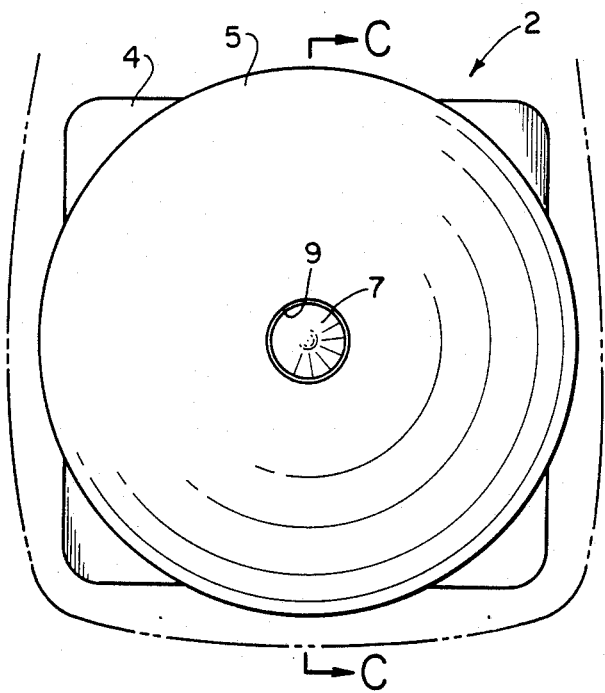

Turning now to the specific embodiments of the invention, FIG. 1C depicts device 2 as having a substantially square base 4 and a circular protective element, or cushion, 5. Irritating element, or pin, 7 is accomodated within opening 9 in cushion 5 and is attached to base 4. As best seen in FIG. 1B, base 4 has a flat portion from which extends a column 11. The shape of cushion 5 is shown to be rounded so as to have a smooth outer surface 25. Cushion 5 includes a recess 13 adjacent to and having a diameter larger than opening 9 (see FIG. 1D). The recess narrows to form a lip 15 which is in contact with flange 17 of column 11. Spring 19 is in compression between surface 21 of recess 13 and face 23 of base 4. Pin 7 is a thin member, like a wire, with a rounded tip. The tip should be made sharp enough to irritate the tongue upon contact but not so as to prick or cut the tongue or otherwise cause actual pain. The thickness of surface 25 surounding opening 9 is sufficient to act as a guide for the cushion as it moves along pin 7. The cushion is also guided by lip 15 sliding along column 11 and by flange 17 sliding within recess 13. The parts are suitably dimensioned to contact each other so as to provide this guiding function. Also, the bore of opening 9 should closely approximate the diameter of pin 7 to form a relatively tight fit and, thereby, to exclude particles of food from recess 13.

Manufacture of device 2 in accordance with this embodiment is accomplished by fabricating base 4 from metal or hard plastic in a well known manner. It can be manufactured to include column 11 or the two can be separate parts attached to each other. Pin 7 is attached to the base in a well-known manner such as by bonding means. The pin can be made from any suitable material such as metal or plastic and its tip shaped as discussed above. Spring 19 is placed over pin 7 and inserted into column 11. Then the assembly is completed by manually deforming the free end of column 11 so it can be forced through lip 15 into recess 13 of cushion 5. Optionally, the surfaces of flange 17 and lip 15 can be suitably beveled (not shown) so that axial force applied to the cushion compresses column 11 to snap flange 17 into recess 13. Once inside recess 13, column 11 returns to its original shape and then flange 17 in cooperation with lip 15 prevent the parts from separating. The cushion is preferably formed from a hard material such as metal or plastic. Each side of the base measures 4.0 mm, cushion 5 has a 4.5 mm diameter, and the height of the device is 2.5 mm.

In use, spring 19 biases cushion 5 to extend away from base 4 up to the limits of movement imposed by the opposed contacting surfaces of lip 15 and flange 17. In this position, the outer surface 25 of cushion 5 is flush with the tip of pin 7. Thus, when the tongue bears lightly against surface 25, it feels only a smooth surface. However, should the tongue thrust forward with sufficient force to overcome the bias of spring 19, cushion 5 will slide to uncover the tip of pin 7 which, in turn, will be projected into the tongue. The resulting discomfort will induce withdrawal of the tongue backward and upward into the mouth to a position where the irritation is removed. After repeated cycles of thrust, discomfort, and withdrawal, the individual becomes educated in the sense that his tongue is trained to assume the proper position at rest and to move correctly during swallowing.

Figures 2A, 2B:
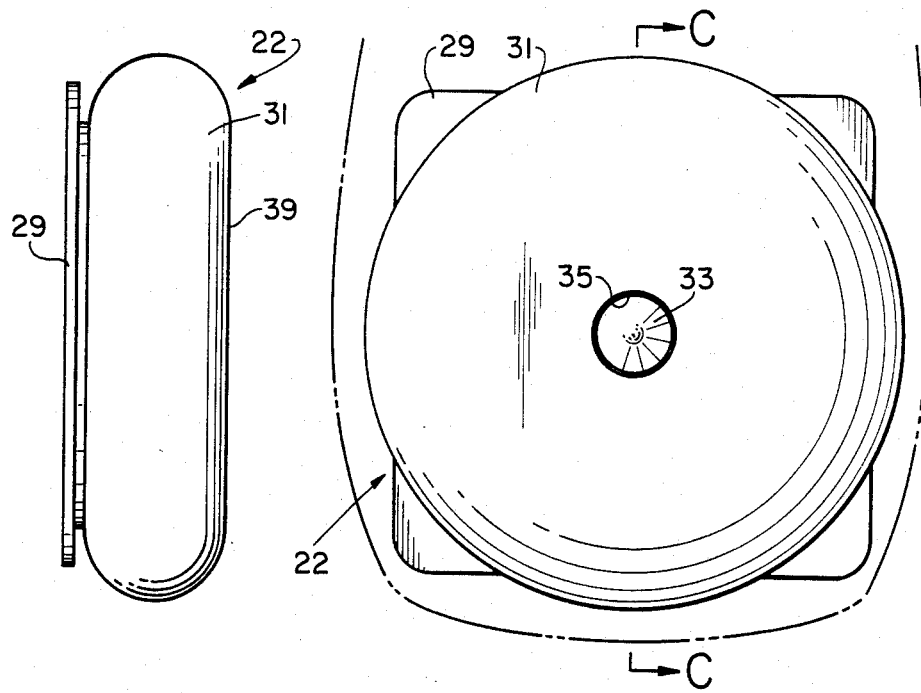
FIGS. 2A, 2B, and 2C show, respectively, the side, elevational and cross-sectional (along line c—c of FIG. 2B) views of a second embodiment of the invention.
Figure 2C:
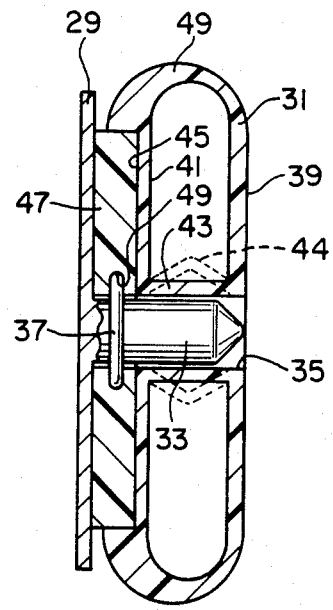

The FIG. 2 (for the sake of convenience, use here and below of only one digit refers collectively to its corresponding figures A, B, C) embodiment includes a square base 29 and a circular protective element, or cushion, 31. Irritating element, or pin, 33 is accomodated within opening 35 in cushion 31. Cushion 31 has a smooth outer shell and an upper surface 39 which is substantially flat (see FIG. 2A). As best seen in FIG. 2C, pin 33 is attached at one end to base 29. A ring 37 is attached to pin 33 near base 29 and is useful for securing the various parts together, as discussed below. Cushion 31 includes top 39 and a bottom 41 joined by a resiliently yieldable circular wall 43. Bottom 41 of the cushion includes a recessed portion 45 facing base 29. Attached within recess 45 is a member 47 having a groove 49 which receives therein the ring 37 on pin 33. The bore of opening 35 closely approximates the diameter of pin 33 to exclude food particles from the device. Also, the pin acts as a guide when cushion 31 is deformed, as discussed below.

Assembly of the device involves attaching pin 33 to base 29 in a well known way. Pin 33 may be a wire-like element to which ring 37 is attached, or the two can be fabricated to form a unitary body. Ring 37 is hard and unyieldable. Cushion 31 is designed to be resilient and is consequently formed of an elastomer or metal spring with suitable properties to yield under anticipated tongue thrusts as well as survive in the type of environment found in the mouth. Wall 43 can be tube-like, as shown, or it can be pre-bent (pleated) as shown in dotted lines and designated by 44 to enhance the yielding property. Member 47 need not have the same properties as the material used for cushion 31, but it must be capable of yielding somewhat so that ring 37 can enter groove 49. Completion of the asembly requires insertion of pin 33 into opening 35 until member 47 contacts the ring. Force is then applied to snap the ring into the groove. Of course, it should be understood that optionally ring 37 can be made of an elastomer while member 47 is some type of hard material. The dimensions of this embodiment are the same as those of the previous embodiment, except that the height of the device is 2.0 mm.

In use, the tip of pin 33 is normally flush with surface 39 of the cushion. However, the cushion can be deformed under the above-described thrusting action of the tongue. The deformation occurs at side 49 and wall 43 to compress the height of the cushion and move surface 39 toward base 29 to, thereby, expose the tip of pin 33. Wall 43 (or 44) is also compressed but travels at its top and bottom along pin 33 acting as a guide therefor. As described with respect to the previous embodiment, in such a circumstance pin 33 will cause sufficient discomfort to induce the tongue to withdraw away from the teeth carrying the device.

An advantageous aspect of this embodiment lies in having a fully enclosed device. This prevents or at least minimizes the collection of food and bacteria inside the device where it would be difficult or impossible for the individual to clean.

Device 32 shown in FIG. 3 includes a square base 51 on which is mounted protective element, or cushion, 53. Irritating element, or pin, 55 is accomodated within opening 57 in cushion 53. As best shown in FIG. 3C, pin 55 is a wire-like element while opening 57 is a hole which extends through cushion 53 from top 59 to base 51. The bore of hole 57 closely approximates the diameter of pin 55. Cushion 53 is formed from an elastomeric material to provide resilience and it contains a plurality of voids 63 which contribute to the yieldability and resilience characteristics of the cushion. A void-filled foam material would be suitable, for example. Cushion 53 also includes a cavity 65 with lip 61 which cooperates with rim 67 on base 51 in assembly of the device. The outer dimensions of this embodiment are the same as those of the FIG. 2 embodiment.

Device 32 is assembled by forming base 51 to include rim 67 in a well known manner. Likewise, well known, conventional techniques are available for fabricating cushion 53 to include voids 63 and cavity 65 with lip 61. To assemble the parts, cushion 53 is brought toward base 51 so that pin 55 moves into opening 57 until lip 61 contacts rim 67. At that point, the bottom is stretched over the rim and force is exerted to cause lip 61 to snap over rim 67.

In use, when the device is installed on the lingual side of a tooth, pin 55 has its tip flush with surface 59 of the cushion. As in the previously disclosed embodiments, pressure from the tongue will cause deformation of the cushion and the consequent irritation of the tongue by pin 55. Like the FIG. 2 embodiment, this one also has a fully enclosed interior arrangement with its attendant advantages.

Device 42 in FIG. 4 is another embodiment of the invention. On square base 69 is mounted circular protective element, or cushion, 71. Irritating element, or pin 73, is accomodated within opening 75 in cushion 71. Cushion 71 is hollow with a flat top surface 77 and a bottom lip 79. Lip 79 cooperates with rim 81 on base 69 to secure the parts together after assembly. Cushion 71 is formed of a material with the resilience and other properties suitable for this usage. This material could be elastomeric or metal. In one version, this cushion material along provides the requisite attributes of yielding under tongue pressure and then springing back to its original shape after the tongue is withdrawn. An alternative approach is to include in device 42 a spring 82 and a washer 83. The spring is compressed between base 69 and surface 84 of washer 83. Neck 86 of washer 83 lies within opening 75. Thus, the bore of opening 75 closely approximates the outer diameter of neck 86 while the inner diameter closely approximates the pin diameter. The resulting fit permits movement of the part as necessary but excludes food particles from the interior of cushion 71.

Assembly of device 42 proceeds by placing spring 82 over pin 73 and then slipping the washer over the pin as well. Cushion 71 is then brought toward base 69 with pin 73 and washer 83 being inserted into opening 75. In this position, lip 79 is pressing against rim 81. The lip portion is stretched over the rim and some force is exerted to press the rim into the cushion. Of course, should no spring be used, then only lip 79 of cushion 71 is pressed unto rim 81.

In use, the description above relative to the previously described embodiments applies here as well. Furthermore, this embodiment has an enclosed interior with its attendant advantages.

FIG. 5 depicts device 52 as including a square base 85 upon which is mounted protective element, or cushion, 87. Irritating element, or pin, 89 is accomodated within opening 91 of cushion 87. Opening 91 is defined by a neck portion 107 of top surface 93, and has a bore closely approximating the diameter of pin 89. The cushion is hollow and includes a rounded top surface 93 and a bottom lip 95. The cushion preferably is formed of an elastomeric material. Lip 95 cooperates with flange 97 on base 85 to secure the cushion to the base. In particular, internal ring 99 on the lip 95 fits into external groove 101 on flange 97. As in the previous embodiment just discussed above, cushion 87 can alone function to provide the resilient properties required. However, alternatively it can be spring-biased by spring 103 compressed between base 85 and washer 105. Washer 105 bears against neck portion 107 of cushion 87. Dimensionally, this embodiment is the same as that of FIG. 1.

Device 52 is fabricated by providing base 86 with a flange 97 made of a suitable hard material such as metal or plastic. The cushion is manufactured in the shape shown in accordance with well known, conventional methods. Likewise, the wire-like pin 89 is attached to the base in conventional fashion. Should use of a spring be selected, spring 103 is placed on pin 89 and washer 105 is pushed onto the spring. Cushion 87 is brought toward base 85 by inserting pin 89 into opening 91. In this position, lip 95 presses against flange 97. To complete the assembly operation, lip 95 is stretched and force is exerted to snap ring 99 into groove 101.

In use, the description above with regard to the previous embodiments applies here as well. This embodiment is also of the fully enclosed type and benefits from its attendant advantages.

Figure 6A:
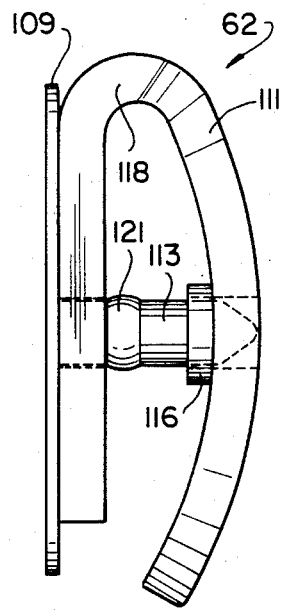
FIGS. 6A, 6B, and 6C show, respectively, the side, elevational and cross-sectional (along line c—c of FIG. 6) views of a sixth embodiment of the invention.
Figure 6B:
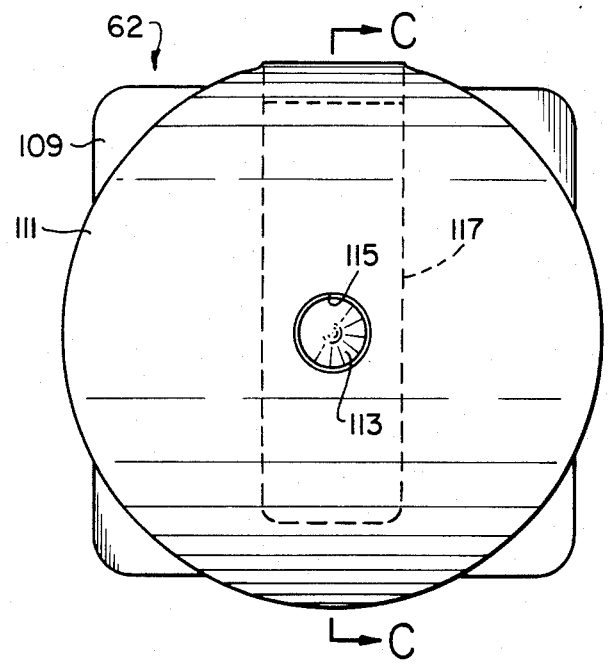
Figure 6C:
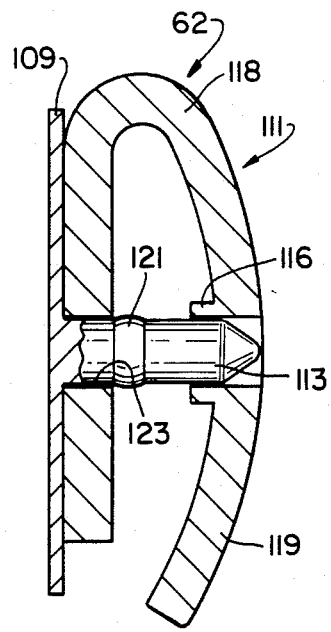

Device 62 in FIG. 6 includes a square base 109 upon which is mounted protective element 111. Protective element 111 is in the shape of a leaf spring with a mounting bracket 117 and rounded top surface 119 connected at resilient portion 118. Irritating element, or pin, 113 is accomodated within opening 115 in cushion 111. Opening 115 is defined by neck 116 of surface 119. Bracket 117 and pin 113 are attached to base 109. Pin 113 includes a ring 121 near the point of its attachment to the base. In fact, the location of ring 121 corresponds to the thickness of bracket 117. Bracket 117 includes a hole 123 through which pin 113 extends to the base. Spring 111 is made of a resilient material, such as metal, an elastomer, or plastic. The outer dimensions of this embodiment are the same as those of the FIG. 1 embodiment.

Assembly of device 85 is accomplished by attaching pin 113 to base 109 in any well known manner. The already suitably fabricated spring 111 is lowered onto pin 113 by inserting the pin through hole 123 in bracket 117 and then pressing on the bracket to force ring 121 through hole 123. In this position, the pin will, of course, also extend into opening 115. With ring 121 bearing tightly against bracket 117, the parts are held securely in place.

In use, surface 119 is normally flush with the tip of pin 113. However, under tongue pressure, surface 119 will be forced to move toward base 109 thereby exposing the pin.

Device 72 shown in FIG. 7 is similar to device 62 in FIG. 6 in that it also uses a leaf-spring type of protective element, 125, mounted on a base, 127. However, they differ in the means for attaching the various parts to each other. Bracket 128 of spring 125 is attached to the base in a well known manner, such as by bonding or gluing. The bracket includes a tapped hole 129 into which the threaded portion of pin 131 is screwed. Pin 131 includes a nut 133 as a part thereof which is useful in tightening the pin to the bracket. The tip of pin 131 is received in opening 135 of top surface 137 of the spring 125.

To assemble device 72, spring 125 is first attached to base 127. Top surface 137 of the spring is then swung away from the bracket just enough to admit pin 131 and place it into hole 129. The pin is then turned and tightened. Once this operation is complete, top surface 137 of the spring is released and it returns to its original position thereby receiving the head of pin 131 in opening 135.

The use of this device is the same as that described above for device 62.

Figure 8A:
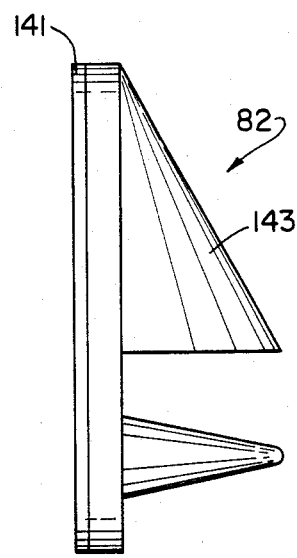
FIGS. 8A, 8B, and 8C show, respectively, the side, elevational and cross sectional (along line c—c of FIG. 8B) views of an eighth embodiment of the invention.
Figure 8B:
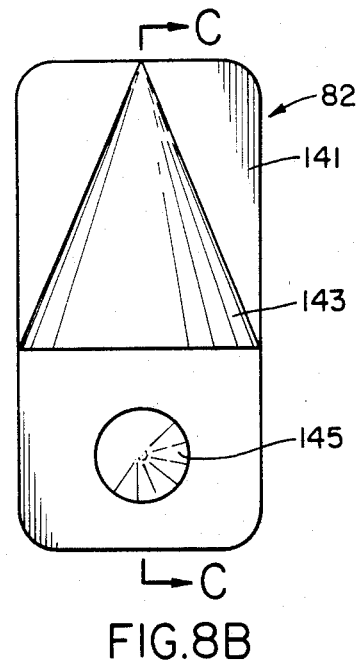
Figure 8C:
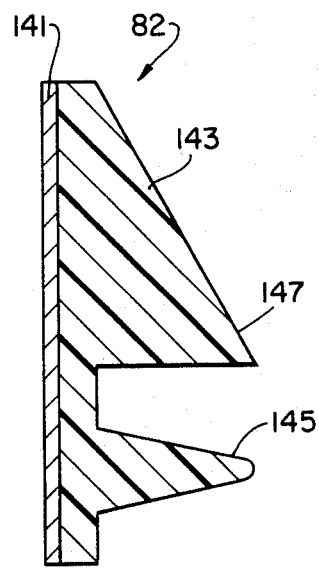

Device 82 depicted in FIG. 8 requires no moving parts to provide the desired tongue therapy results. Mounted on a rectangular base 141 is protective element 143 and irritating element 145. The protective element is a ramp having an angled surface 147 which is closest to base 141 at one end of the base and then slopes away from the base. The shape of the ramp is depicted as preferably conical. In fact, it is shown in the shape of a cone sliced in half with its tip at one end of the base. However, the ramp can likewise have a top surface which has a uniform width throughout. Also, top surface 147 can be curved rather than straight. The essential feature of the ramp lies in creating some resistance to the downward movement of the tongue along the tooth. Irritating element 145 is preferably also conical in shape and is attached to base 141 just below ramp 147.

Device 82 can be formed of the three separate parts attached by well known means. Alternatively, it can be shaped from a single piece, also by well known means. Also, more than one irritating element can be mounted below the ramp.

In use, the device is mounted on the lingual surface of a tooth as described above with regard to the other embodiments. The tongue, which takes a path toward the teeth from above the teeth, must first traverse ramp 143. Because ramp 143 is shaped so that it slopes out into the mouth, the tongue will encounter resistance as it attempts to move outward and downward. In other words, as the tongue thrusts forward and down toward the teeth, ramp 143 forces it backward if it is to move downward. This resistance should normally keep the tongue away from element 145. However, if the thrust exceeds a certain level, the tip of the tongue will move over the ramp and beyond until it touches element 145 and senses the resultant irritation.

Each of the above-disclosed embodiments can be manufactured in quantity because of the uniformity possible when a custom fit for each inidividual is not required. If the teeth encountering the problem are the upper incisors, for example, the base of the device is securely affixed to the flat, lingual side of the incisor with an adhesive which permits its removal when desired. Proper fit is inherent since the devices are small enough to fit on the tooth. The compact size minimizes interference with eating and other wearer discomfort. Because each device fits only on one tooth and no connections are required among teeth or among devices, fitting the devices to an individual, installation and removal are relatively fast and easy. As shown in FIG. 1A, the devices are preferably placed away from the gums so that no irritation due to the devices themselves or any food particles temporarily collected therein is likely.

It should be understood that although specific embodiments of the invention have been described in detail above, various modifications will be readily apparent. For example, although the irritating element has been described throughout the above disclosure as a member having a pointed end, the source of irritation might be, for example, a chemical substance on its tip or even the completion of an electrical circuit which would give a very small shock to the patient or would trigger a buzzer to alert the patient to improper tongue movement. Also, the cushions have been described as circular but another outline, such as elliptical, rectangular, oval, etc., can also be used. These and other such modifications are intended to be included within the scope of the invention as defined by the following claims.

I claim:

1. A tongue therapy device to prevent tongue thrust during swallowing and to train the tongue to assume its proper posture on the palate comprising:
   a base having one face adapted for attachment to the lingual side of a tooth;
   a tongue irritating element attached to the other, lingual face of said base; and
   a protective element means associated with said tongue irritating element and mounted on said base to keep the tongue away from the irritating element until the tongue extends beyond a given position in the mouth said protective element means having a normal position and a displaced position, the protective element means preventing the irritating element from contacting the tongue in said normal position, and said irritating element being contactable by the tongue in the displaced position of said protective element means.

2. The device of claim 1, wherein the protective element means is and has a normal position and a displaced position, the protective element covering the irritating element in said normal position, and said irritating element being contactable by the tongue in the displaced position of said protective element.

3. The device of claim 2, wherein the irritating element comprises a pin attached at one end to said base and extending substantially perpendicular thereto.

4. The device of claim 3, wherein the protective element means comprises a cushion having a bottom surface and a top surface with a hole therein for receiving said pin, said top surface being flush with the tip of said pin in the normal position of the protective element means.

5. The device of claim 4, whrein the diameter of said pin and the bore of said hole closely approximate each other to form a close fit which permits relatively free sliding movement therebetween.

6. The device of claim 5, wherein the cushion is spring biased relative to said base.

7. The device of claim 6, wherein the cushion includes a recess defined by walls extending radially away from said pin and axially from near said top surface through to the bottom surface and forming a radial lip at the bottom surface, and further including a column extending perpendicularly away from and attached to said base surrounding said pin, said column having a flange at its free end inside said recess and in opposed engagement with said lip.

8. The device of claim 7, wherein said lip is slidable on said column and said flange is slidable along said recess wall.

9. The device of claim 5, wherein the cushion is elastomeric.

10. The device of claim 9, wherein the elastomeric cushion is hollow except for a tube between its top and bottom surfaces defining said hole.

11. The device of claim 10, further comprising a ring attached to said pin, and wherein the bottom surface of said cushion includes a groove adjacent said pin for receiving said ring.

12. The device of claim 11, wherein the wall of said tube is folded to enhance its yieldability.

13. The device of claim 12, wherein the bottom surface of said cushion includes a recess surrounding said pin and a material in said recess which is less yieldable than said top surface of the cushion, said groove being within said material.

14. The device of claim 9, wherein the elastomeric cushion is a void-filled foam.

15. The device of claim 14, wherein the elastomeric cushion is fully enclosed except for an opening in the bottom surface forming a lip thereon, and further including a rim attached to said base extending into said cushion in opposed engagement with said lip to secure said cushion to said base.

16. The device of claim 5, wherein said cushion is hollow and fully enclosed except for an opening in its bottom surface forming a lip thereon, and further comprising a rim attached to said base and extending into said cushion in opposed engagement with said lip to secure said cushion to said base.

17. The device of claim 16, wherein the top surface of the cushion is spring biased relative to the base.

18. The device of claim 15, wherein said cushion is elastomeric.

19. The device of claim 5, wherein said cushion is hollow and fully enclosed except for an opening in the bottom surface which includes a lip having an internal ring thereon, said base having a flange attached thereto with an external groove receiving said ring therein.

20. The device of claim 19, wherein the top surface of the cushion is spring biased relative to the base.

21. The device of claim 5, wherein said cushion comprises a spring with said top surface and bottom surface being attached at one resilient portion.

22. The device of claim 20, wherein the pin includes a ring bearing tightly against the bottom surface of said cushion, said bottom surface including a hole through which the pin extends to the base.

23. The device of claim 21, wherein the bottom surface includes a tapped hole and said pin includes a threaded end screwed into said tapped hole.

24. The device of claim 23, wherein said pin includes a nut thereon for tightening said pin.

25. The device of claim 1, wherein the base when mounted on a tooth has an upper end and a lower end, said irritating element being mounted on the lower end and said protective element comprising a top surface which extends from said upper end of the base to the proximity of said irritating element.

26. The device of claim 25, wherein the irritating element is substantially perpendicular to said base.

27. The device of claim 26, wherein the distance from the base to the point on the top surface of said irritating element spaced furthest away from it and the distance from the base to the point on the protective element means spaced furthest away from it are approximately equal.

* * * * *

UNITED STATES PATENT AND TRADEMARK OFFICE
CERTIFICATE OF CORRECTION

PATENT NO. : 4,608,974
DATED : September 2, 1986
INVENTOR(S) : Robert J. Sicurelli, Jr.

It is certified that error appears in the above-identified patent and that said Letters Patent is hereby corrected as shown below:

Column 8, lines 60 - 65 (Claim 2) should read as follows:

2. The device of claim 1, wherein the protective element means is resiliently displaceable.

Signed and Sealed this

Twenty-third Day of December, 1986

*Attest:*

DONALD J. QUIGG

*Attesting Officer*  *Commissioner of Patents and Trademarks*